(12) United States Patent
Paul et al.

(10) Patent No.: US 10,101,290 B2
(45) Date of Patent: Oct. 16, 2018

(54) METHOD FOR DETERMINING THE CONDUCTIVITY OF A MEDIUM

(71) Applicant: Endress+Hauser Conducta GmbH+Co. KG, Gerlingen (DE)

(72) Inventors: Stefan Paul, Döbeln (DE); Erik Münz, Rossau (DE)

(73) Assignee: Endress+Hauser Conducta GmbH+Co. KG, Gerlingen (DE)

( * ) Notice: Subject to any disclaimer, the term of this patent is extended or adjusted under 35 U.S.C. 154(b) by 0 days.

(21) Appl. No.: 15/238,982

(22) Filed: Aug. 17, 2016

(65) Prior Publication Data

US 2017/0052243 A1 Feb. 23, 2017

(30) Foreign Application Priority Data

Aug. 21, 2015 (DE) .................. 10 2015 113 922

(51) Int. Cl.
*G01R 27/08* (2006.01)
*G01R 35/00* (2006.01)
*G01N 27/06* (2006.01)
*G01R 27/22* (2006.01)
*G01R 17/00* (2006.01)

(52) U.S. Cl.
CPC .............. *G01N 27/06* (2013.01); *G01R 17/00* (2013.01); *G01R 27/22* (2013.01); *G01R 35/005* (2013.01)

(58) Field of Classification Search
CPC ....... G01R 35/005; G01R 27/22; G01N 27/06
USPC .................................................. 324/693, 601
See application file for complete search history.

(56) References Cited

U.S. PATENT DOCUMENTS

2012/0068723 A1 3/2012 Sullivan
2015/0097588 A1* 4/2015 Kim ...................... G01N 27/08
324/693

OTHER PUBLICATIONS

Search Report for German Patent Application No. 10 2015 113 922.7, German Patent Office, dated May 23, 2016, 7 pp.

* cited by examiner

*Primary Examiner* — Amy He
(74) *Attorney, Agent, or Firm* — Mark A. Logan; PatServe

(57) ABSTRACT

The present disclosure relates to a method for determining the conductivity of a medium by means of a conductive conductivity sensor, comprising the steps of determining measured values of the conductivity sensor, determining reference measured values of a reference circuit integrated into the conductivity sensor, deriving at least one adjustment value from the reference measured values of the reference circuit, and correcting the measured values of the conductivity sensor by means of the at least one adjustment value.

11 Claims, 1 Drawing Sheet

METHOD FOR DETERMINING THE CONDUCTIVITY OF A MEDIUM

CROSS-REFERENCE TO RELATED APPLICATION

The present application is related to and claims the priority benefit of German Patent Application No. 10 2015 113 922.7, filed on Aug. 21, 2015, the entire contents of which are incorporated herein by reference.

TECHNICAL FIELD

The present disclosure relates to a method for determining the conductivity of a medium by means of a conductive conductivity sensor.

BACKGROUND

A conductivity sensor includes a measuring circuit for measuring the electrical conductivity of a medium based upon a resistance measurement of the medium and the subsequent calculation with a factor that is referred to as a cell constant and results from the geometry of the conductivity sensor. Typically, the measuring circuits for a conductivity sensor are adjusted during the production. In the process, errors, such as amplification and zero point errors, are determined, and correction values, if any, are stored in the non-volatile memory. Such an adjustment usually occurs at room temperature, since a change in the temperature is difficult to implement during the adjustment. Such a conductivity sensor is operated at the customer's premises for a time period of many years and is there exposed to various environmental conditions, such as humidity and temperature fluctuations.

The correction values for the measuring circuit are determined at a point in time when defined environmental conditions, such as temperature, prevail. As a result of molding of the measuring circuit from, for example, epoxy resin, temperature fluctuations, or aging over a long period of operation, deviations in the measuring chain of the measuring circuit can occur. These deviations may possibly impair the specified measurement precision of the conductivity sensor.

BRIEF SUMMARY OF THE INVENTION

The present disclosure includes a method for determining the conductivity of a medium by means of a conductive conductivity sensor with high measurement precision.

The object of the present disclosure is a method for determining the conductivity of a medium by means of a conductive conductivity sensor, comprising the steps of determining measured values of the conductivity sensor, determining reference measured values of a reference circuit integrated into the conductivity sensor, deriving at least one adjustment value from the reference measured values of the reference circuit, correcting the measured values of the conductivity sensor by means of the at least one adjustment value.

The solution according to the present disclosure is advantageous in that the reference circuit is integrated into the conductivity sensor (on-board adjustment) for automatic adjustment. With suitable algorithms and timed sequences, it is then possible to adjust the conductivity sensor during the measurement operation, to determine correction values and to always ensure an optimal measurement performance.

Another advantage of the on-board adjustment is the diagnosis of malfunctions of certain circuit components. This may be realized by comparing the determined adjustment values with theoretical ideal values for the adjustment. If the determined correction values deviate too much from the theoretical values, a malfunction of the conductivity sensor exists, and the superordinate system may react accordingly.

According to at least one embodiment, a time-controlled alternation between the determination of the measured values of the conductivity sensor and the determination of the reference measured values of the reference circuit takes place. As a result of the cyclical adjustment of the conductivity sensor, medium-term changes of faulty components may be determined and adjusted. For example, the temperature influences on resistors and other components over time can be adjusted thereby.

According to an embodiment, two measured values of the conductivity sensor and, subsequently, one reference measured value of the reference circuit are determined.

According to another embodiment, the conductivity sensor comprises an electronic circuit with at least two measurement ranges. The electronic circuit is able to select its measuring range from the at least two measurement ranges by selecting an internal resistance of the electronic circuit. The selection of the internal resistance allows the electronic circuit to best match its internal resistance with the expected resistance of the medium to obtain the best measurement precision. An active measurement range is the range (i.e., the internal resistance) currently in use by the electronic circuit for conductivity measurements. During a measurement, adjustments are made more frequently in the active measurement range than in the other measurement range(s).

Since the electronic circuit may have several measurement ranges, it is expedient to adjust the currently active measurement range more frequently, in order to ensure the highest precision and best performance. If the other measurement ranges were, however, ignored, inaccuracies could occur over a longer period of time. This would, in particular, be the case if the temperature of the electronic circuit were to change while a measurement range is active. If the change to a different measurement range occurs at that time, the adjustment value would no longer be current in this range, and incorrect measured values would be determined. After a certain period of time, the error would be minimized, since the other measurement ranges are also adjusted.

BRIEF DESCRIPTION OF THE DRAWINGS

The described embodiments and other features, advantages and disclosures contained herein, and the manner of attaining them, will become apparent and the present disclosure will be better understood by reference to the following description of various exemplary embodiments of the present disclosure taken in conjunction with the accompanying drawings, wherein.

Figure 1:
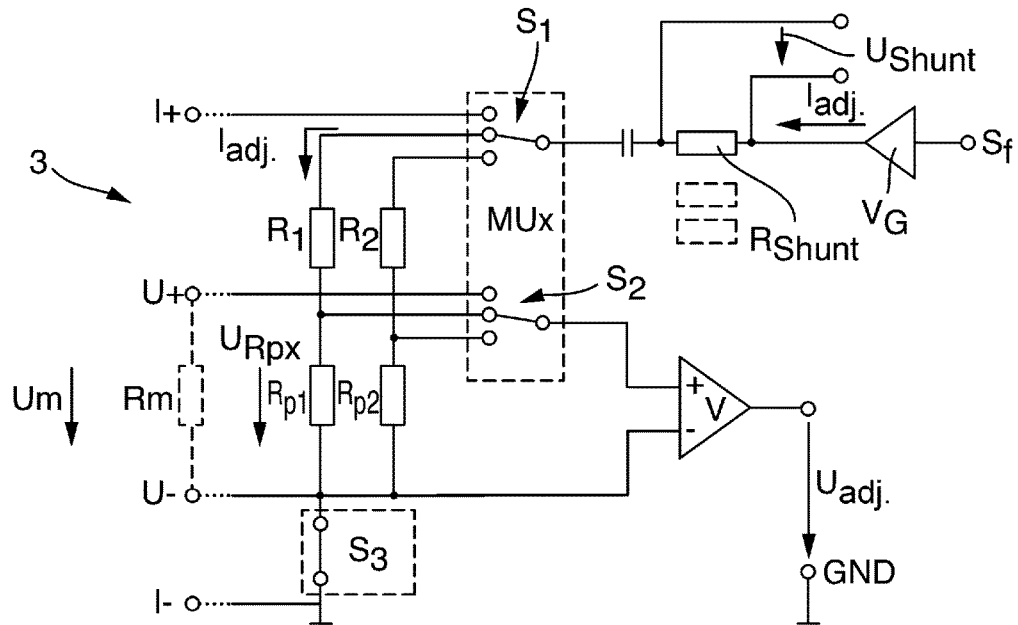
FIG. 1 shows a measuring circuit for measuring conductivity with an integrated reference circuit according to exemplary embodiments of the present disclosure.

Like reference numerals indicate the same or similar parts throughout the several figures. It should be appreciated that not all of the features of the components of the figures are necessarily described. Some of these non-discussed features, such as various fasteners, etc., as well as discussed features are inherent from the figures. Other non-discussed features may be inherent in component geometry or configuration.

DETAILED DESCRIPTION

FIG. 1 shows a measuring circuit 3 for measuring conductivity with an integrated reference circuit. The measuring circuit 3 is operated by means of a signal generator (not shown) that provides a signal $S_f$ with a frequency f. A generator amplifier VG amplifies the signal $S_f$ and generates an adjustment current $I_{adj}$. The adjustment current $I_{adj}$ flows through a shunt resistor $R_{shunt}$ and generates a shunt voltage $U_{shunt}$. If the shunt voltage $U_{shunt}$ and the shunt resistor $R_{shunt}$ are known, the adjustment current $I_{adj}$ can be determined:

$$I_{adj.} = \frac{U_{shunt}}{R_{shunt}}$$

Through the shunt resistor $R_{shunt}$, the adjustment current $I_{adj}$ flows to a multiplexer MUX that comprises two switches $S_1$ and $S_2$. Both switches $S_1$, $S_2$ comprise three positions and are synchronized, which means that if the top switch $S_1$ is in the center position, the bottom switch $S_2$ is also in the center position, etc. Connected to the MUX are voltage dividers, one voltage divider including the resistors $R_1$ and $R_{p1}$, the other voltage divider including the resistors $R_2$ and $R_{p2}$. If both switches $S_1$, $S_2$ are in the center position, the adjustment current $I_{adj}$ flows through voltage divider $R_1$ and $R_{p1}$ via a third closed switch $S_3$ to ground and generates a voltage $U_{Rpx}$ along $R_{p1}$:

$$U_{Rpx} = R_{p1} \cdot I_{adj.}$$

The voltage $U_{Rpx}$ is amplified by means of an amplifier V, wherein the amplification factor v is determined as follows:

$$v = \frac{U_{adj.}}{U_{Rpx}}$$

If the resistors $R_{shunt}$ and $R_{p1}$ are dimensioned as follows:

$$R_{shunt} = 100\Omega\ R_{p1} = 390\Omega,$$

and if, for example, the following values are measured for the shunt voltage $U_{shunt}$ and the adjustment voltage $U_{adj}$:

$$U_{shunt} = 100\ mV\ U_{adj} = 2\ V,$$

then the result for $I_{adj}$, $U_{Rpx}$, and v is:

$$I_{adj.} = \frac{U_{shunt}}{R_{shunt}} = \frac{100\ mV}{100\ \Omega} = 1\ mA$$

$$U_{Rpx} = R_{p1} \cdot I_{adj.} = 390\ \Omega \cdot 1\ mA = 390\ mV$$

$$v = \frac{2\ V}{0.39\ V} = \underline{5.128}$$

If both switches of the multiplexer MUX are in the top position, the adjustment current $I_{adj}$ flows via two current electrodes I+, I− through the medium, and a measured value of the conductivity sensor is determined. The current electrodes I+ and I−, together with the two voltage electrodes U+, U−, constitute the four poles of the four-terminal measurement of the conductivity sensor. During the measurement of the medium, the switch $S_3$ is open and connected to a separate ground, so that the voltage electrode U− is not short-circuited with the current electrode I−.

If the medium between the voltage electrodes U+ and U− is represented by a medium resistance $R_m$, the voltage $U_m$ between the voltage electrodes U+ and U− decreases. The current $I_m$ (not shown in the drawing) is regulated until the current $I_m$ through the medium is equal to the adjustment current $I_{adj}$ (see above). In this example, the following values were measured for the shunt voltage $U_{shunt}$ and the adjustment voltage $U_{adj}$, after the switches were changed from the center to the top position:

$$U_{shunt} = 80\ mV\ U_{adj} = 1\ V$$

Thus, the medium resistance $R_m$ can be determined as follows, by means of the amplification factor v=5.128:

$$I_m = \frac{U_{shunt}}{R_{shunt}} = \frac{80\ mV}{100\ \Omega} = 0.8\ mA$$

$$U_m = \frac{U_{adj.}}{v} = \frac{1\ V}{5.128} = 195\ mV$$

$$R_m = \frac{U_m}{I_m} = \frac{0.195\ V}{0.8\ mA} = \underline{243.76\ \Omega}$$

With an on-board adjustment, the conditions are, therefore, adjusted exactly in the same way as they are adjusted in a medium measurement (amplitude, frequency, shunt resistor, amplification). The goal of the adjustment is the calculation of the amplification factor v of the amplifier V. With the adjustment current $I_{adj}$, the ideal voltage drop $U_{Rpx}$ through the resistor $R_{p1}$ can be calculated. With the measured adjustment voltage $U_{adj}$, the amplification factor v can be calculated. The amplification factor v compensates for all errors of the measuring circuit 3. If the current flow is subsequently directed through the medium again, the same conditions prevail as during the adjustment of the measurement range. However, the current flow is corrected or adjusted by means of the determined amplification factor v.

As shown by the dashed-line boxes below $R_{shunt}$ hunt in FIG. 1, the measuring circuit 3 may use optional values for $R_{shunt}$ to effect different measurement ranges. That is, the selection of a measurement range is effected by selecting a value for $R_{shunt}$ to be used by the measuring circuit 3. For example, if it is expected the medium resistance $R_m$ will be low, a measurement range will be selected such that the selected $R_{shunt}$ will obtain the most precise measurements in the high conductive medium. Likewise, if it is expected the medium resistance $R_m$ will be high, a measurement range will be selected such that the selected $R_{shunt}$ will obtain the most precise measurements in the low conductive medium. Therefore, the active measuring range, i.e., the measuring range to be used by the conductivity sensor during a medium measurement, will be selected based on the expected resistance/conductivity of the medium to be measured.

Figure 2:
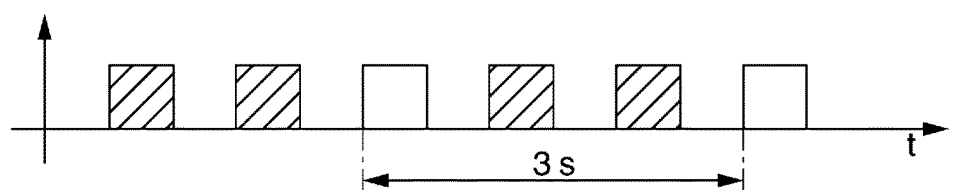
FIG. 2 depicts a sequence of medium and adjustment measurements according to exemplary embodiments of the present disclosure.

FIG. 2 shows a sequence of medium and adjustment measurements. The medium and adjustment measurements each last for half a second and occur once per second each. One adjustment measurement follows two medium measurements.

Figure 3:
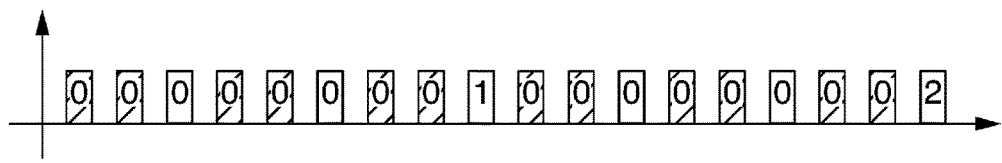
FIG. 3 depicts a sequence of medium and adjustment measurements in various measurement ranges according to exemplary embodiments of the present disclosure.

FIG. 3 shows a sequence of medium and adjustment measurements in accordance with FIG. 2, in which the medium and adjustment measurements occur in different measurement ranges 0, 1, and 2. The measurement range 0, in which the current conductivity measurement occurs, is adjusted more frequently than the measurement ranges 1 and 2. If the measurement range is changed from 0 to 1, the adjustment values for measurement range 1 are available and can be provided immediately, in order to ensure optimal measurement performance.

The invention claimed is:

1. A method for determining a conductivity of a medium using a conductive conductivity sensor, comprising:
   determining measured values of the conductivity sensor in a first measurement range using a measurement circuit integrated into the conductivity sensor;
   determining reference measured values in the first measurement range using a reference circuit integrated into the conductivity sensor;
   determining reference measured values in a second measurement range using the reference circuit integrated into the conductivity sensor;
   deriving a first adjustment value from the reference measured values in the first measurement range;
   deriving a second adjustment value from the reference measured values in the second measurement range;
   correcting the measured values of the conductivity sensor using the first adjustment value; and
   determining the conductivity of the medium using the corrected measured values.

2. The method according to claim 1, further comprising:
   alternating between determining the measured values of the conductivity sensor in the first measurement range and determining the reference measured values in the first measurement range in a time-controlled manner.

3. The method according to claim 2, further comprising:
   determining two measured values of the conductivity sensor in the first measurement range and subsequently determining one reference measured value in the first measurement range.

4. The method according to claim 1, wherein the determining of reference measured values in the first measurement range
   is performed more frequently than the determining of reference measured values in the second measurement range.

5. The method of claim 1, further comprising:
   selecting the second measurement range of the conductivity sensor;
   determining second measured values in the second measurement range using the measurement circuit;
   correcting the second measured values of the conductivity sensor using the second adjustment value; and
   determining the conductivity of the medium in the second measurement range using the corrected second measured values.

6. The method of claim 5, wherein selecting the second measurement range includes selecting a second resistance of a selectable resistor of an amplifier circuit of the measuring circuit.

7. The method of claim 1, further comprising:
   determining reference measured values in a third measurement range using the reference circuit integrated into the conductivity sensor; and
   deriving a third adjustment value from the reference measured values in the third measurement range.

8. The method of claim 7, further comprising:
   selecting the third measurement range of the conductivity sensor;
   determining third measured values in the third measurement range using the measurement circuit;
   correcting the third measured values of the conductivity sensor using the third adjustment value; and
   determining the conductivity of the medium in the third measurement range using the corrected third measured values.

9. The method of claim 8, wherein selecting the third measurement range includes selecting a third resistance of a selectable resistor of an amplifier circuit of the measuring circuit.

10. A conductivity measuring circuit, comprising:
    a first amplifier circuit including a selectable resistance, the first amplifier circuit configured to supply an electrical current;
    a second amplifier circuit having a first input and a second input and configured to amplify an input voltage across the first input and the second input and to output the amplified input voltage via an output of the second amplifier circuit;
    a first switch, wherein the first switch is single-pole, triple-throw;
    a second switch, wherein the second switch is single-pole, triple-throw, and wherein the first switch and the second switch are configured to operate synchronously;
    a first reference circuit including a resistor $R_1$ and a resistor $R_{p1}$ forming a first voltage divider, a first end of the first reference circuit connected to the first switch and a second end of the first reference circuit connected to the second input of the second amplifier circuit, wherein the first reference circuit is connected between $R_1$ and $R_{p1}$ to the second switch;
    a second reference circuit including a resistor $R_2$ and a resistor $R_{p2}$ forming a second voltage divider, a first end of the second reference circuit connected to the first switch and a second end of the second reference circuit connected to the second input of the second amplifier circuit, wherein the second reference circuit is connected between $R_2$ and $R_{p2}$ to the second switch;
    a first electrical contact embodied to contact a liquid medium, the first electrical contact connected to the first switch;
    a second electrical contact embodied to contact the liquid medium, the second electrical contact connected to the second switch;
    a third electrical contact embodied to contact the medium, the third electrical contact connected to the second input of the second amplifier circuit; and
    a fourth electrical contact embodied to contact the medium, the fourth electrical contact connected to a ground,
    wherein when the first switch and the second switch are each in a first position, the first switch connects an output of the first amplifier circuit to the first electrical contact and the second switch connects the second electrical contact to the first input of the second amplifier circuit,
    wherein when the first switch and the second switch are each in a second position, the first switch connects the output of the first amplifier circuit to the first end of the first reference circuit and the second switch connects the first reference circuit between $R_1$ and $R_{p1}$ to the first input of the second amplifier circuit,
    wherein when the first switch and the second switch are each in a third position, the first switch connects the output of the first amplifier circuit to the first end of the second reference circuit and the second switch connects the second reference circuit between $R_2$ and $R_{p2}$ to the first input of the second amplifier, and wherein the selectable resistance of the first amplifier circuit is selected to correspond to an expected resistance of the medium.

11. The conductivity measuring circuit of claim 10, wherein when the first switch and the second switch are each in the first position, the first amplifier circuit is configured to pass an electrical current through the medium via the first electrical contact and the fourth electrical contact, and the second amplifier circuit is configured to amplify a voltage difference in the medium between the second contact and the third contact and to output the amplified voltage difference via the second amplifier circuit output, wherein when the first switch and the second switch are each in the second position, the first amplifier circuit is configured to pass an electrical current through the first reference circuit, and the second amplifier circuit is configured to amplify a voltage across $R_{p1}$ and to output the amplified voltage across $R_{p1}$ via the second amplifier circuit output, and wherein when the first switch and the second switch are each in the third position, the first amplifier circuit is configured to pass an electrical current through the second reference circuit, and the second amplifier circuit is configured to amplify a voltage across $R_{p2}$ and to output the amplified voltage across $R_{p2}$ via the second amplifier circuit output.

* * * * *